United States Patent [19]

Shanley et al.

[11] Patent Number: 5,359,669
[45] Date of Patent: Oct. 25, 1994

[54] REMOTE RETINAL SCAN IDENTIFIER

[75] Inventors: Charles W. Shanley, Lake Zurich, Ill.; Karen Jachimowicz, Goodyear; Michael S. Lebby, Chandler, both of Ariz.

[73] Assignee: Motorola, Inc., Schaumburg, Ill.

[21] Appl. No.: 867,958

[22] Filed: Apr. 13, 1992

[51] Int. Cl.⁵ .............................................. G06K 9/00
[52] U.S. Cl. .......................................... 382/6; 382/2; 382/1; 351/205
[58] Field of Search ............ 382/2, 1, 6; 351/205, 351/211, 209; 359/196, 298; 345/7

[56] References Cited

U.S. PATENT DOCUMENTS

| | | | |
|---|---|---|---|
| 4,109,237 | 8/1978 | Hill | 382/2 |
| 4,393,366 | 7/1983 | Hill | 382/2 |
| 4,620,318 | 10/1986 | Hill | 382/2 |
| 4,641,349 | 2/1987 | Flom et al. | 382/2 |
| 4,993,068 | 2/1991 | Piosenka et al. | 340/825.34 |
| 5,000,562 | 3/1991 | Ichihashi et al. | 351/221 |
| 5,202,929 | 4/1993 | Lemelson | 382/2 |

FOREIGN PATENT DOCUMENTS 0306874 12/1989 Japan .

*Primary Examiner*—Leo H. Boudreau
*Assistant Examiner*—Chris Kelley
*Attorney, Agent, or Firm*—Eugene A. Parsons

[57] ABSTRACT

An identifier which scans the retina of an eye, senses the magnitude of reflections and transmits signals representative of the magnitudes to a remote location which stores the signals and compares them to previously stored magnitude signals for purposes of identifying the eye and, hence, the owner of the eye. The equipment can alternatively be used to produce a direct written image on the retina. Combining the two provides a secure communication system.

8 Claims, 3 Drawing Sheets

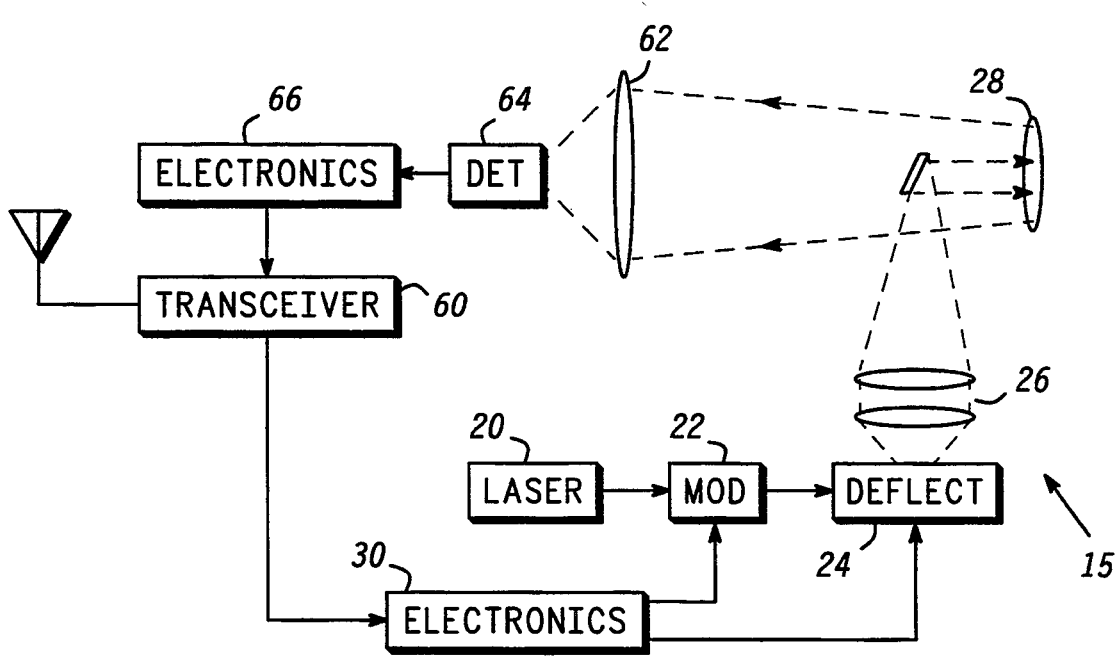
FIG. 1
FIG. 2
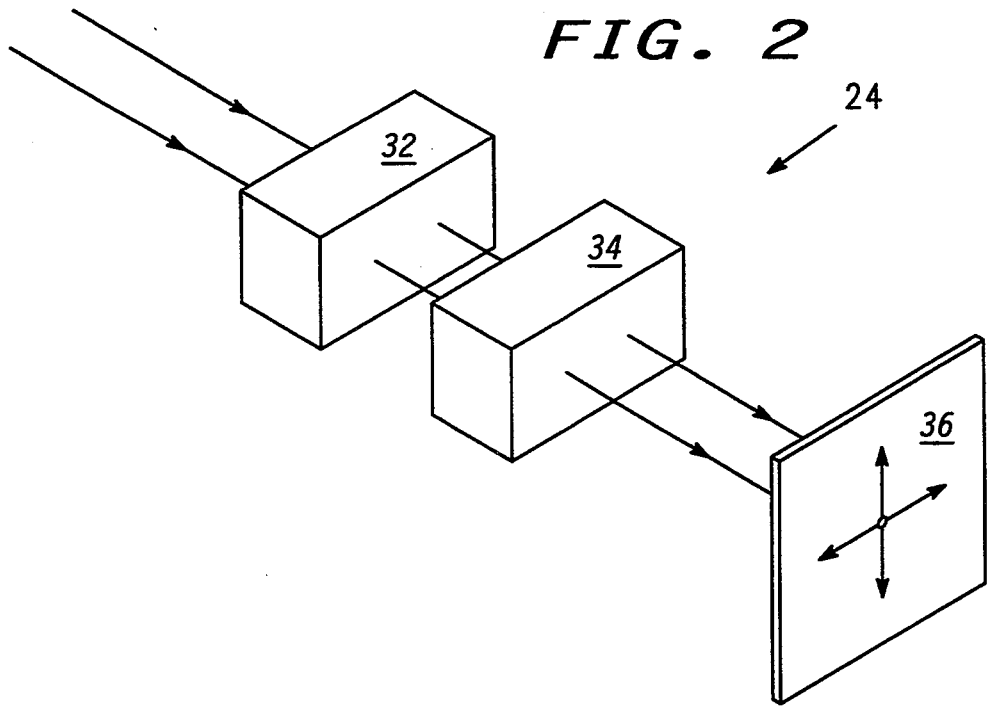

FIG. 5
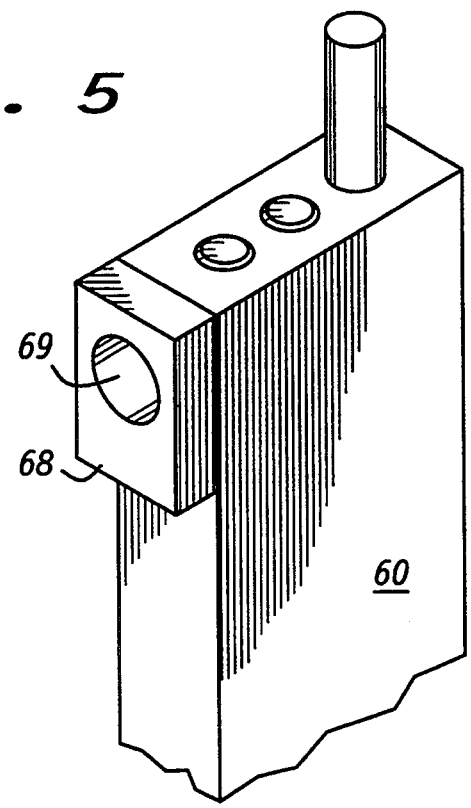
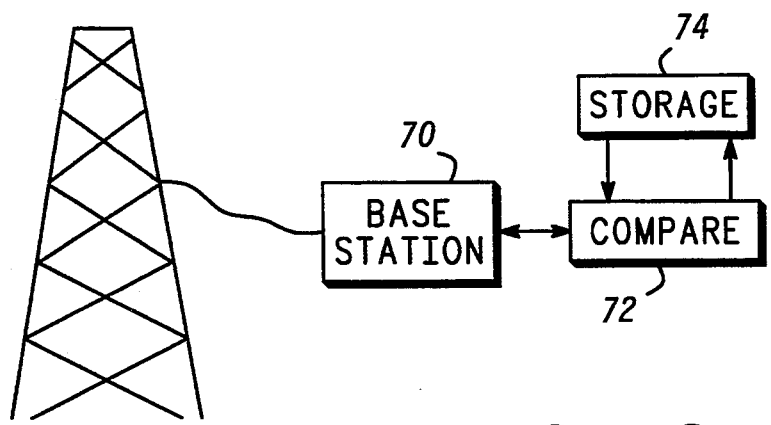
FIG. 6

REMOTE RETINAL SCAN IDENTIFIER

The present invention pertains to identification and security systems and more specifically to a remotely positioned retinal scan identifier.

BACKGROUND OF THE INVENTION

It is known that the retinal reflectivity of an eyeball is different for each eyeball and may be used for identification purposes, similar to fingerprints. Generally, a retinal identifier is a relatively large and complicated device requiring a large memory and apparatus (a computer or the like) for comparing the retinal reflectivity information to stored information. Because of the size and power requirements, retinal identifiers can only be used in very limited applications where size, power, etc. are not a factor to be considered.

SUMMARY OF THE INVENTION

It is a purpose of the present invention to provide a new and improved remote retinal scan identifier.

It is a further purpose of the present invention to provide a new and improved remote retinal scan identifier which is smaller and requires less power than prior identifiers and can easily be incorporated into portable equipment for identification of or by the operator.

It is a further purpose of the present invention to provide a method of remotely identifying the retina of a human eye.

The above problems are solved and purposes realized by a remote retinal scan identifier including a light source forming a directed beam of light, deflection means positioned to receive the beam of light for scanning the beam of light over a retina, electronic means coupled to the deflection means for controlling the deflection means to scan the retina, a detector positioned to receive reflected light from the scanned retina and provide output signals indicative of the magnitude of reflected light, and a communication transmitter coupled to the detector to receive the output signals from the detector and transmit the output signals to identification apparatus remote from the communication transmitter.

The above problems are solved and purposes realized by a method of providing remote retinal scan identification including the steps of providing a directed beam of light, deflecting the beam of light to scan the beam of light over a retina, detecting the magnitude of light reflected from the retina, and transmitting a signal indicative of the magnitude of reflected light to a remote receiver having identification apparatus connected thereto.

BRIEF DESCRIPTION OF THE DRAWINGS

Referring to the drawings:

FIG. 1 is a block diagram of a remote retinal scan identifier and video imaging apparatus in accordance with the present invention;

FIG. 2 is a view in perspective of a specific deflection system for the apparatus of FIG. 1;

FIG. 5 is a view in perspective of a portable communication transceiver incorporating the apparatus of FIG. 1;

FIG. 6 is a block diagram of a remote base station constructed to communicate with the transceiver of FIG. 5;

DESCRIPTION OF THE PREFERRED EMBODIMENT

Figure 3:
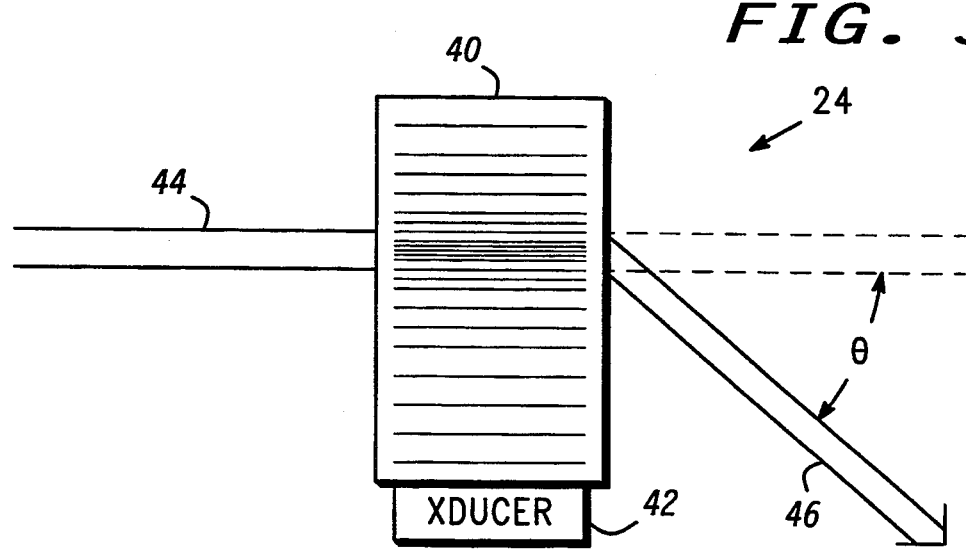
FIG. 3 is a detailed optical ray diagram of a portion of the deflection system of FIG. 2.

FIG. 1 is a block diagram of a remote retinal scan identifier and video imaging apparatus 15 in accordance with the present invention. A laser 20, which may be any of the well known lasers including solid state lasers, such as vertical cavity surface emitting lasers, diode lasers, diode-pumped lasers, etc., supplies a coherent light beam to a modulator 22. Modulator 22, when activated, impresses video information onto the light beam generally by modulating the intensity of the light beam as, for example, by providing changes in the power level of laser 20. Depending upon the application, the modulation could be as simple as turning laser 20 off and on, which essentially translates into a digital system. Acousto-optic modulators are one of the preferred modulators for most applications, but other techniques, such as electro-optics and mechanical are completely feasible. Modulator 22, in this specific embodiment operates to allow the direct passage (unmodulated) of the light beam from laser 20 therethrough when modulator 22 is deactivated.

The modulated/unmodulated light beam from modulator 22 is directed to a deflection system 24. A lens system 26 is used to focus the light beam from deflection system 24 into the retina of an eye 28. The focal length of lens system 26 is chosen so that the focal point of the scanning optical system is at the pupil of eye 28, and the focal point of the beam optical system is at the retina of eye 28. The purpose of deflection system 24 is to scan the modulated/unmodulated light beam on the retina of eye 28 in a regular pattern, such as a rastor. There are many possible configurations for deflection system 24 and lens system 26, depending upon the application of apparatus 10 and how it is desired to scan the retina of eye 28.

FIG. 2 illustrates one embodiment of a specific deflection system 24. In FIG. 2, deflection system 24 includes an acousto-optic horizontal scanner 32 and an acousto-optic vertical scanner 34 which in combination produce a moving spot of light on a retina or, for purposes of explanation, screen 36. Acousto-optic components are small, solid state crystals which are used for deflecting laser beams and the like. In this specific embodiment scanners 32 and 34 are constructed similarly and one is oriented orthogonal to the other. Since scanners 32 and 34 are constructed similarly, only one scanner will be discussed in detail.

Referring to FIG. 3, an optical ray diagram of scanner 32 is illustrated, along with basic components incorporated into scanner 32. An acousto-optic crystal 40 has a transducer 42 mounted thereon for applying a variable pressure thereto generally perpendicular to a light beam 44 impinging thereon. As is known in the art, as evidenced, for example, by the following article and book: Lekavich, J. (1986), Basics of Acousto-Optic Devices, *Lasers Appl.*, April; 59-64 and Yariv, A. and P. Yeh (1984), *Optical Waves in Crystals,* Wiley, New York crystal 40 is constructed so that variations in the index of refraction occur generally perpendicular to light beam 44 as pressure variations are applied to crystal 40. In general, the angle $\theta$ is dependent upon the frequency of the signal applied to transducer 42 so that the exact angle of deflection is easily controlled electronically. As transducer 42 changes the index of refraction of crystal 40 in one direction (upwardly in FIG. 3), light beam 44 is deflected downwardly, as illustrated by solid arrow 46. As transducer 42 changes the index of refraction of crystal 40 in the opposite direction, light beam 44 is slowly deflected in the opposite direction (upwardly in FIG. 3). Thus, transducer 42 can be controlled electronically to cause light beam 44 to trace a line in one direction.

Scanner 34 is constructed to receive light beam 46 from scanner 32 and deflect light beam 46 in a direction orthoganal to the direction that scanner 32 deflects it. Thus, scanners 32 and 34 cooperate to move the light spot produced on screen 36 in any desired direction or to any desired position. It should be noted that the acousto-optic crystal in scanner 34 may be somewhat more complicated, or larger, than crystal 40, since the light beam will already be deflected when it is received by scanner 34. Since the image written on the retina is less than 0.5 inches on a side, the amount of movement of the beam at scanners 32 and 34 is very small and, therefore, this difference in size is very small. In applications where size is not a problem the crystals will be similar in size and construction, for easy standardization.

While there are several possible techniques for scanning, or writing, an image on the retina, probably the simplest is to scan a complete raster (rectangularly shaped image area) on the retina at regular intervals. The regular intervals must be sufficiently fast so that it appears to the eye to be a continuous image, which means that a complete scan must be made approximately 60 times per second. To provide this raster, crystal 40 is controlled by transducer 42 to scan light beam 44, generally linearly, in a straight line at a first frequency. The crystal in scanner 34 is controlled by its transducer to slowly scan light beam 44 in a direction orthogonal to the direction swept by crystal 40. Thus, each time crystal 40 scans a complete line the crystal of scanner 34 moves the beam sufficiently so that the next scan is parallel with and adjacent the previous scan. In this way a complete rastor is scanned periodically. To insure safety of the retina of eye 28, the laser light entering eye 28 lies in the range of approximately 10 to 100 microwatts.

Figure 4:
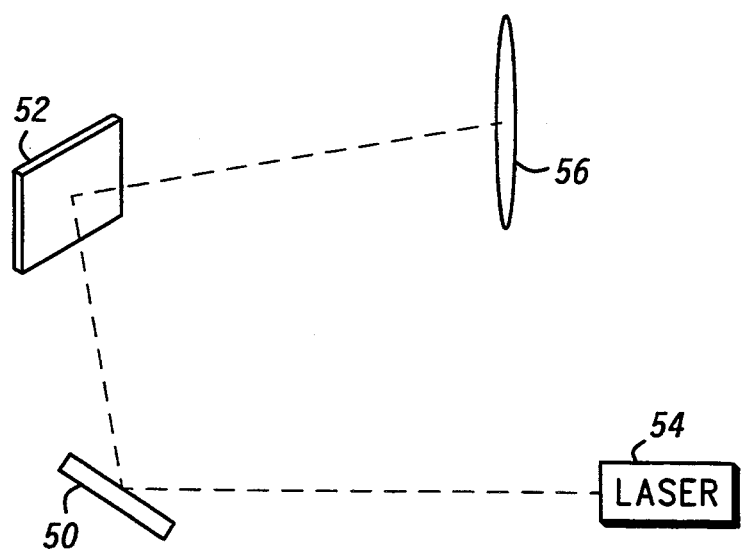
FIG. 4 is a view in perspective of a another specific deflection system for the apparatus of FIG. 1.

FIG. 4 is a view in perspective of another specific deflection system for apparatus 24 of FIG. 1. The deflection system of FIG. 4 includes a first mirror 50 and a second mirror 52. Mirror 50 is situated to receive a beam of light from a light source, such as laser 54, and scan the beam of light in a horizontal line. Mirror 52 is situated to receive the horizontally scanned beam of light and scan it in an orthogonal, or in this specific example, a vertical direction and to direct the light beam into eye 56. Thus a complete rastor scan is available at eye 56. Mirrors 50 and 52 are very small and consume low electrical power, such small galvanometer mirrors, or micro-machined mirrors. It will of course be understood that any combination of the various deflection systems can be used, if desired, for specific applications.

In one mode of operation apparatus 15 writes an image directly on the retina of eye 28. To produce an image, modulator 22 must be controlled to vary the intensity of light beam 44 so that, as light beam 44 is swept through a complete raster, spots of different light intensity combine to form an image. Timing and control of modulator 22 and deflection system 24 is provided by electronics 30. Electronics 30 includes a basic oscillator, or timer, which provides the timing signals to cause the sweeping and modulating to occur at the proper times. Also, electronics 30 provides video signals to modulator 22 to modulate light beam 44 to the correct intensity at the required times. Further, electronics 30 provides horizontal and vertical (orthogonal) deflection signals to cause deflection system 24 to periodically scan light beam 44 in a rastor. Depending upon the application and the desired image resolution, the horizontal deflection frequency may be on the order of 15 to 30 KHz., the vertical deflection is no lower than 60 Hz., and the modulating frequency may be on the order of 12 MHz.

Electronics 30 receives she video information from a communications transceiver 60 constructed to receive the video information, along with audio or other information, from a base station or another remotely located transceiver, either of which will hereinafter be referred to simply as a base station for convenience. In this fashion the operator communicates with the remote base station and apparatus 15 provides the operator with substantially any video information, e.g., images photographs, maps, etc., that the remote base station desires to transmit.

In another mode of operation apparatus 15 scans the retina of eye 28 and reflected light is focused by an optical lens system 62 onto a light detector 64. In this mode, modulator 22 is deactivated so that the intensity of the scanned light beam remains substantially constant as the light beam is swept through a complete rastor. As is known in the art, the reflectivity pattern of the retina of eye 28 causes variations in the magnitude of light received by detector 64. Electronics 66 receives the output of detector 64 and converts it into a signal capable of being transmitted by transceiver 60. Transceiver 60 transmits the signal representative of the reflectivity of the retina of eye 28 to a remote base station such as base station 70 in FIG. 6. A typical example of how a remote retinal scan identifier is incorporated into a portable transceiver 60 is illustrated in FIG. 5. In FIG. 5, all of apparatus 15, except transceiver 60 is included in a housing 68 affixed to one side of portable transceiver 60. An opening 69 is provided for placing the eye to allow scanning thereof.

Referring specifically to FIG. 6, base station 70 includes comparison apparatus 72, which in this specific embodiment is a computer dedicated to the process of comparing the reflectivity of retinas for identification purposes, and storage apparatus 74, which in this embodiment is a hard disc associated with the computer and which may be facilitated by floppy discs and the like. When base station 70 receives retina reflectivity information from transceiver 60, the information is stored in storage apparatus 74 and then compared to all previous stored information to arrive at a match and, hence, an identification of the retina and the person whose eye is being scanned. Once an identification is made this information is immediately transmitted back to transceiver 60 for the benefit of the operator of apparatus 15.

It should be noted that there are at least two primary uses for the remote retinal scan identifier, neither use being possible in previous equipment. First, apparatus 15 can be used by police, fire personnel, medical personnel, etc. to identify otherwise unidentifiable (or questionable) individuals. The policeman etc. simply notifies base station 70 that he is sending retinal scan information and then has the unidentified person look into opening 69 to allow scanning of his retina. The reflectivity information is transmitted to base station 70 where the retina, and owner, are identified and the identification information is immediately returned to the policeman, etc.

In a second major potential application, transceiver 60 is used for secure communications. In this application the operator contacts the base station and then looks into opening 69 so that reflectivity information is automatically transmitted to base station 70. If the retinal scan correctly identifies the operator the communication may then be completed. If an incorrect or unidentifiable operator has control of transceiver 60 communication with that transceiver is simply terminated.

Thus, a new and improved remote retinal scan identifier is disclosed which scans the retina of an eye and transmits reflectivity information to a remote station for identification in a first mode of operation and "writes" a display produced from remotely transmitted video information directly onto the retina of the eye in a second mode of operation. Because the identification is made remotely and the display is directly written, very low power is required and the size and complexity of the apparatus is substantially reduced. Also, because of the very small size and extremely low power utilized, the apparatus is more convenient and useful than prior identifiers and/or displays.

While we have shown and described specific embodiments of the present invention, further modifications and improvements will occur to those skilled in the art. We desire it to be understood, therefore, that this invention is not limited to the particular forms shown and we intend in the append claims to cover all modifications that do not depart from the spirit and scope of this invention.

What is claimed is:

1. A combination remote retinal scan identifier and direct retinal scan display comprising:
    a light source, including a laser, forming a directed beam of light;
    deflection means positioned to receive the beam of light for scanning the beam of light over at least a portion of a retina, the deflection means including reflecting surfaces moveably mounted to direct the light beam generally in two orthogonal directions;
    modulating means positioned to receive the directed light beam from the light source for modulating the light beam with video information prior to the deflection means receiving the light beam;
    electronic means coupled to the deflection means and the modulating means for controlling the deflection means and the modulating means to scan a video image on the retina;
    a detector positioned to receive reflected light from the scanned retina and provide output signals indicative of the magnitude of reflected light; and
    a communication transmitter coupled to the detector to receive the output signals from the detector and transmit the output signals to identification apparatus remote from the communication transmitter; and
    electronics coupled to the modulating means and the detector for activating the detector and deactivating the modulator means during remote retinal scan identifying and for deactivating the detector and activating the modulating means to produce a direct retinal scan display.

2. A combination remote retinal scan identifier and direct retinal scan display as claimed in claim 1 wherein the laser light entering the eye lies in the range of approximately 10 to 100 microwatts.

3. A combination of remote retinal scan identifier and direct retinal scan display as claimed in claim 1 wherein the deflection means includes deflection means moveably mounted to direct the light beam generally in two orthogonal directions and the deflection means and the electronics coupled thereto cooperate to can a rastor on the retina during remote retinal scan identification and to produce a direct retinal scan display.

4. A remote retinal scan identifier as claimed in claim 1 including in addition a base station with a receiver tuned to receive the transmitted output signals, storage means for storing received output signals, and comparator means for comparing received output signals to stored output signals.

5. A combination remote retinal scan identifier and direct retinal scan display as claimed in claim 1 wherein the modulating means includes an acousto-optic modulator.

6. A combination remote retinal scan identifier and direct retinal scan display as claimed in claim 1 wherein the modulating means includes a mechanical modulator.

7. A combination remote retinal scan identifier and direct retinal scan display comprising:
    a communication receiver designed to receive video information transmitted by a remote transmitter;
    a laser positioned to provide a collimated directed beam of light;
    deflection means positioned to receive the beam of light for scanning the beam of light over a retina;
    a lens system positioned to receive the beam of light from the deflection system and focus the beam of light on the retina of an eye of an operator;
    modulating means positioned to receive the directed light beam from the laser for modulating the light beam with video information prior to the deflection means receiving the light beam, the modulating means being coupled to the communication receiver so that video information received by the communication receiver is supplied to the modulating means;
    electronic means coupled to the deflection means for controlling the deflection means to scan at least a portion of the retina;
    a detector positioned to receive reflected light from the scanned retina and provide output signals indicative of the magnitude of the reflected light;
    a communication transmitter coupled to the detector to receive the output signals from the detector and transmit the output signals, the communication receiver and the communication transmitter being incorporated into a portable transceiver; and
    a base station with a receiver tuned to receive the transmitted output signals and further including storage means coupled to the receiver for storing received output signals, and comparator means coupled to the receiver and the storage means for comparing received output signals to stored output signals to identify the retina; and
    electronics coupled to the modulating means and the detector for activating the detector and deactivating the modulator means during remote retinal scan identifying and for deactivating the detector and activating the modulating means to produce a direct retinal scan display.

8. A combination remote retinal scan identifier and direct retinal scan display as claimed in claim 7 wherein the modulating means includes an acousto-optic modulator.

* * * * *